US011235113B2

(12) United States Patent
O'Callaghan et al.

(10) Patent No.: US 11,235,113 B2
(45) Date of Patent: Feb. 1, 2022

(54) DEVICE AND METHOD FOR MONITORING ADHERENCE TO INHALED THERAPY (71) Applicants: Chris L. O'Callaghan, West Langton (GB); Xiao Liu, London (GB)

(72) Inventors: Chris L. O'Callaghan, West Langton (GB); Xiao Liu, London (GB)

(73) Assignees: UNIVERSITY COLLEGE LONDON, London (GB); UCL BUSINESS PLC, London (GB)

( * ) Notice: Subject to any disclaimer, the term of this patent is extended or adjusted under 35 U.S.C. 154(b) by 672 days.

(21) Appl. No.: 16/092,343

(22) PCT Filed: Apr. 7, 2017

(86) PCT No.: PCT/EP2017/058461
§ 371 (c)(1),
(2) Date: Oct. 9, 2018

(87) PCT Pub. No.: WO2017/174807
PCT Pub. Date: Oct. 12, 2017

(65) Prior Publication Data
US 2019/0160237 A1 May 30, 2019

Related U.S. Application Data (60) Provisional application No. 62/320,084, filed on Apr. 8, 2016.

(51) Int. Cl.
A61M 15/00 (2006.01)
A61B 5/087 (2006.01)
(Continued)

(52) U.S. Cl.
CPC ....... A61M 15/0086 (2013.01); A61B 5/0878 (2013.01); A61B 5/4839 (2013.01);
(Continued)

(58) Field of Classification Search
CPC ............ A61M 15/0086; A61M 15/009; A61M 15/0065; A61M 11/06; A61M 16/024;
(Continued)

(56) References Cited

U.S. PATENT DOCUMENTS 6,981,499 B2    1/2006  Anderson
10,810,283 B2 * 10/2020 Shetty .................... G16H 10/60
(Continued)

FOREIGN PATENT DOCUMENTS

CN      203724572 U    7/2014
JP      2013-517082 A  5/2013

OTHER PUBLICATIONS

International Search Report dated Jul. 7, 2017 issued in PCT/EP2017/058461.

Primary Examiner — Manuel A Mendez
(74) Attorney, Agent, or Firm — Scully, Scott, Murphy & Presser, P.C.

(57) ABSTRACT

A device for monitoring adherence of a patient to a prescribed regimen is provided. The device has a pulmonary delivery device fluid, an adapter in communication with the delivery device and a dispenser in fluid communication with the adapter. A pressurized drug, contained in the pulmonary delivery device, can be delivered from the pulmonary delivery device to the patient through the adapter and the dispenser. A sensor is mounted to the adapter or the dispenser for detecting a temperature or pressure change caused by the movement of the drug from the pulmonary delivery device to the patient and generating a feedback signal based on the change. The feedback signal is further processed for generating a signal indicating a successful deliver of the drug to the patient.

17 Claims, 9 Drawing Sheets (51) Int. Cl.
 *A61B 5/00* (2006.01)
 *G16H 20/10* (2018.01)
(52) U.S. Cl.
 CPC ... *A61M 15/009* (2013.01); *A61M 2205/3331* (2013.01); *A61M 2205/3368* (2013.01); *A61M 2205/3546* (2013.01); *A61M 2205/3576* (2013.01); *A61M 2205/50* (2013.01); *G16H 20/10* (2018.01)
(58) Field of Classification Search
 CPC ............ A61M 15/008; A61M 16/0069; A61M 15/0091; A61M 16/0051
 See application file for complete search history.

(56) References Cited

U.S. PATENT DOCUMENTS

| | | | |
|---|---|---|---|
| 2006/0130838 A1* | 6/2006 | Lee | A61M 15/0086 128/205.23 |
| 2012/0285236 A1 | 11/2012 | Haartsen et al. | |
| 2013/0008436 A1 | 1/2013 | Von Hollen et al. | |
| 2016/0325058 A1* | 11/2016 | Samson | A61B 5/087 |
| 2021/0045657 A1* | 2/2021 | Thomas | A61M 15/0086 |

* cited by examiner

DEVICE AND METHOD FOR MONITORING ADHERENCE TO INHALED THERAPY

FIELD OF THE DISCLOSURE

The present disclosure relates to an apparatus and method for monitoring a patient's adherence to a therapy of treating diseases, particularly, an inhaled therapy for treating Chronic Obstructive Pulmonary Disease (COPD) and Asthma.

BACKGROUND

It has been consistently documented that poor adherence to a prescribed inhaled therapy has led to detrimental outcome. For example, non-adherence of a prescribed inhaled medicine regimen has resulted in an estimate that it is the fourth highest cause of death in the United States. In England alone, it has been estimated that the direct cost to the National Health Service associated with unused medicine amounts to over 300 million pounds with a concomitant increase of over 500 million pounds per year in healthcare costs arising from failing to adhere to the prescribed treatment. Particularly, with respect to asthma, there are currently 5.4 million people in the United Kingdom receiving treatment for asthma, and it has been estimated that over 130 million pounds per year treatment cost savings can be realized in England, if interventions were made to ensure that all patients were at least 80% adherent to their prescribed regimen. Inhaler therapy forms a major part of treatment of patients with COPD. Therefore, it imperative to contemplate a device and method for ensuring the patients' adherence to a prescribed regimen.

SUMMARY

According to an exemplary aspect of the present disclosure, a device for monitoring adherence of a patient to a prescribed regimen is provided. The device includes a pulmonary delivery device having a pressurized cartridge for accommodating a drug according to the prescribed regimen and a nozzle through which the drug is released. The device further includes an adapter having an inlet, an outlet and a chamber between the inlet and outlet. The inlet is in fluid communication with the nozzle for admitting the drug into the chamber. The chamber is defined by a hollow wall. The device further includes a dispenser coupled with the outlet of the adapter to allow the drug to enter the dispenser from the chamber. The device further includes at least one sensor for detecting a parameter change associated with a movement of the drug from the delivery device to the dispenser and generating a feedback signal based on the parameter change, wherein the feedback signal is processed for generating an indicator signal representative with respect to delivery of the drug to the patient.

DETAILED DESCRIPTION OF EXEMPLARY EMBODIMENTS

Detailed embodiments of the present disclosure are described herein; however, it is to be understood that the disclosed embodiments are merely illustrative of the compositions, structures and methods of the disclosure that may be embodied in various forms. In addition, each of the examples given in connection with the various embodiments is intended to be illustrative, and not restrictive. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the compositions, structures and methods disclosed herein. References in the specification to "one embodiment", "an embodiment", "an example embodiment", and the like, indicate that the embodiment described may include a particular feature, structure, or characteristic, but every embodiment may not necessarily include the particular feature, structure, or characteristic. Moreover, such phrases are not necessarily referring to the same embodiment. The present disclosure is directed to a way of monitoring patient's adherence to the prescribed treatment by a physician.

Figure 1A:
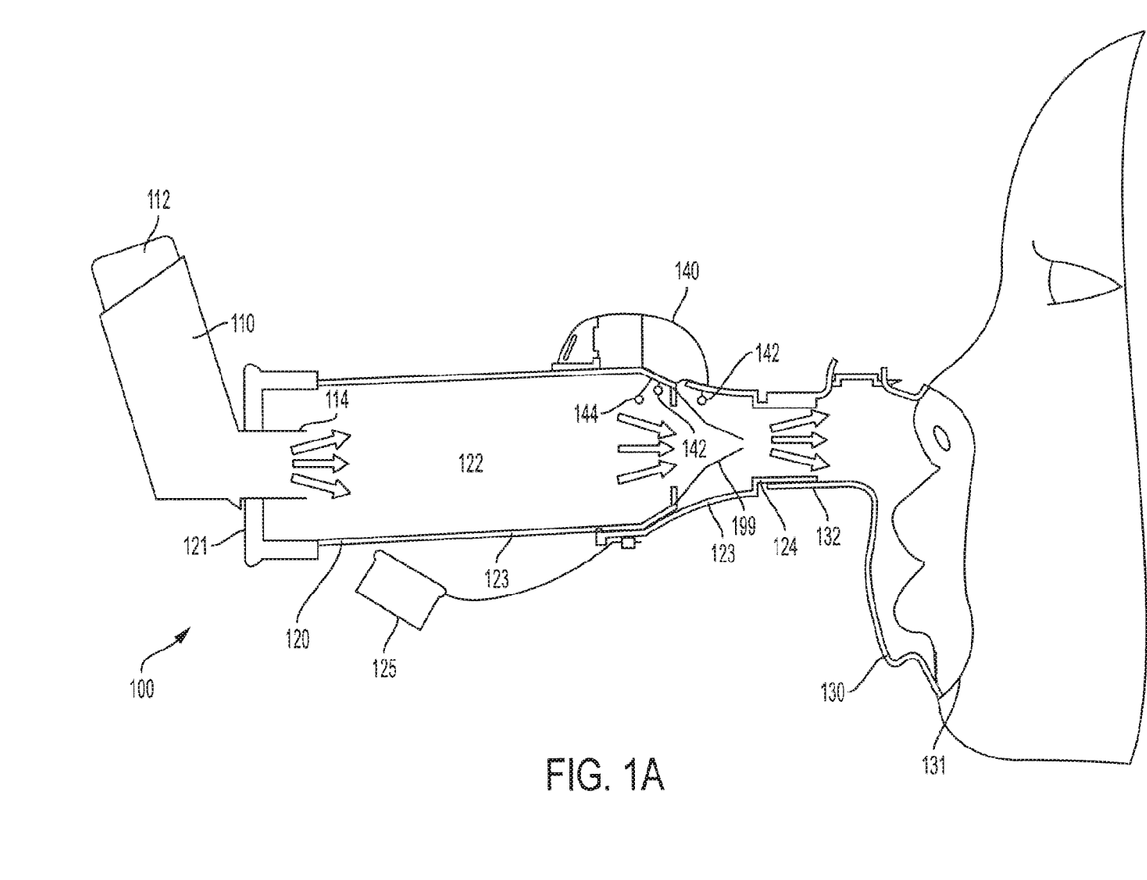
FIG. 1A is a diagram showing a device for monitoring adherence to an inhaled therapy, according to an embodiment of the present disclosure.

FIG. 1A is a schematic diagram showing a device 100 for monitoring adherence to an inhaled therapy. The device 100 includes a pulmonary delivery device 110 for administering medications directly or indirectly to the lungs of a patient. The pulmonary delivery device includes, but is not limited to, atomizers, nebulizers (small volume nebulizers, ultrasonic nebulizers, and vibrating mesh nebulizers), pressurized metered dose inhalers (pMDIs), Dry powder Inhalers (DPIs) and the like). The pulmonary delivery device can also include any type of medical aerosol generators. The pulmonary delivery device can also be any type of pulmonary, nasal, sinus and/or systemic delivery devices.

Asthma and COPD medications may be broken down into two categories: daily preventive treatments, daily treatments and rescue medications. Rescue medications are generally bronchodilators that quickly relax the smooth muscle in the bronchioles in order to dilate the airways and improve ease of breathing during an asthma attack. Rescue medications can have additional properties of drying airway secretions in addition to bronchodilatation. Daily treatments may include anticholinergic agents that are broncholidators and may also dry airway secretions and long acting bronchodilators. Long acting bronchodilators may be given combined with an inhaled steroid administered from the same pressurized metered dose inhaler or in a separate inhaler. Daily preventive treatments typically include anti-inflammatory drugs that reduce the swelling and mucous production in the airways and accordingly reduce a patient's susceptibility to triggers. Preventative anti-inflammatories are effective at controlling and even preventing asthma symptoms. However, preventive treatments are only effective if they are taken consistently at the prescribed times. Generally, adherence by patients to a prescribed regimen of treatment/prevention is difficult to monitor because the medications may be required three times daily, and remission of symptoms due to non-adherence does not usually occur for several days or more. Thus, the delayed feedback in remission removes critical reinforcement to the importance of taking the medication consistently. In addition, many patients may have as many as three different types of inhaled medications, making it confusing and difficult for the patients to follow a prescribed regimen of treatment and making it that more difficult to monitor. Accordingly, asthma treatment adherence is difficult to maintain among asthma patients of all ages, especially in the case of adolescents and children. As a result, non-adherence with the prescribed treatment leads to many attacks and hospitalizations, wasting millions of healthcare dollars year after year. Yet, these can be prevented with an effective means to monitor the adherence of the prescribed medication treatment. The present disclosure is directed to a means of monitoring patients' adherence to the prescribed medication regimen.

Referring to FIG. 1A, the pulmonary delivery device 110 includes one or more pressurized cartridges 112, which a patient actuates by pressing down. The medication is inhaled by the patient, while the medication is sprayed out of a nozzle 114 of the pulmonary delivery device 110. In the case of a child using the facemask, the child can inhale and exhale from a facemask at which point the medication is actuated into the device. However, for some children using the facemask and for older children and adults not using the facemask who inhaled via the device's mouthpiece, the drug is first actuated into the device and then inhaled. Thus, there is a brief pause between actuation of drug into the device and inhalation.

The device 100 further includes a spacer or adapter 120, which is fluidly coupled with the nozzle 114 of the pulmonary delivery device 110 through an inlet 121 of the spacer 120, for allowing the medication of the pulmonary delivery device 110 to enter a chamber 122 of the spacer 120. The chamber 122 is defined by a hollow wall 123 that tapers toward to an outlet 124 of the spacer 120, through which the pressurized medication exits the spacer 120. The hollow wall 123 can be made of an anti-static material or include one or more layers of anti-static coating. For example, the anti-static coating can be made of a suitable metal. The spacer 120 may include a cap 125 for selectively opening and closing the outlet 124.

Figure 1B:
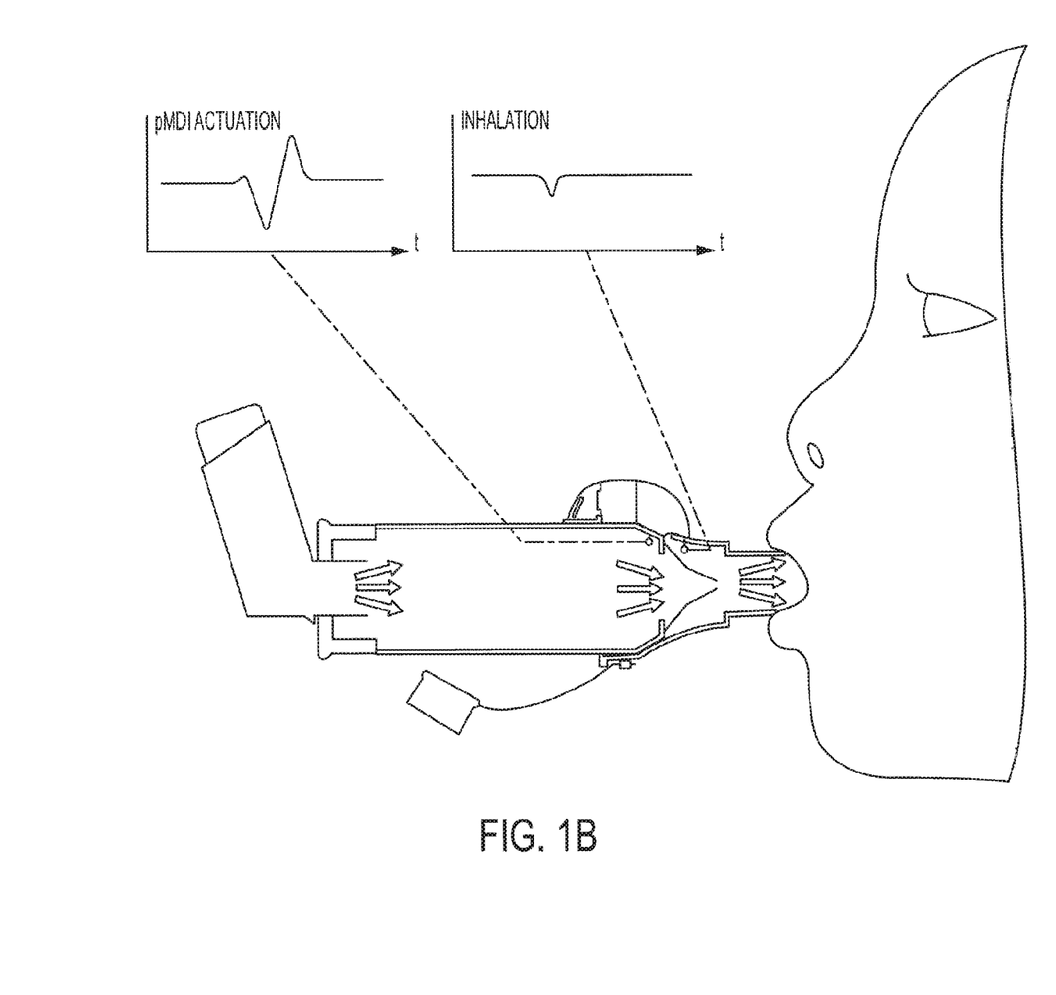
FIG. 1B is a diagram showing a device for monitoring adherence to an inhaled therapy according to another embodiment of the present disclosure.

The device 100 further includes a drug dispenser or accessory 130 for dispensing the medication to the patient. The dispenser 130 includes, but is not limited to, a facemask or a mouth piece. The facemask is typically used by young children, some elderly patients and those who have difficulties coordinating their breathing or inhaling from a mouthpiece. In the shown embodiment, the dispenser is a facemask 130, which has a continuous edge 131. The continuous edge 131 is configured to follow the contour of the patient's face or mouth to provide a relatively snug fit between the facemask and the contour, thereby ensuring that the medication can be properly inhaled by the patient. The facemask 130 further includes an inlet 132, which operatively engages the outlet 124 of the spacer 120 to allow the pressurized medication to enter the facemask 130. The spacer 120 may further include a one-way valve 199, which is attached to the hollow wall 123 for allowing the medication to flow only from the outlet 124 of the spacer to the inlet 132 of the facemask 130. In the embodiment shown in FIG. 1B, a mouthpiece is provided in lieu of the facemask.

The device 100 further includes at least one sensor 140. The device can have one, two, three, four or more sensors thereon. The sensor 140 can be mounted to the wall 123 of the spacer 120. The sensor is in communication with a monitor (receiver) for measuring the parameter(s) detected by the sensor(s) by sending out a signal which is received and monitored by the monitor. In one exemplary embodiment, a sensor array is provided, which includes at first sensor (or a first group of sensors) 142 for detecting a first predetermined parameter and a second sensor (or a second group of sensors) 144 for detecting a second predetermined parameter. For example, the first sensor 142 is a temperature sensor for detecting temperature changes in the chamber 122 of the spacer 120, as the patient breathes; the second sensor 144 is a pressure sensor for detecting pressure changes in the chamber 122 of the spacer 120, as the patient breathes.

Figure 2A:
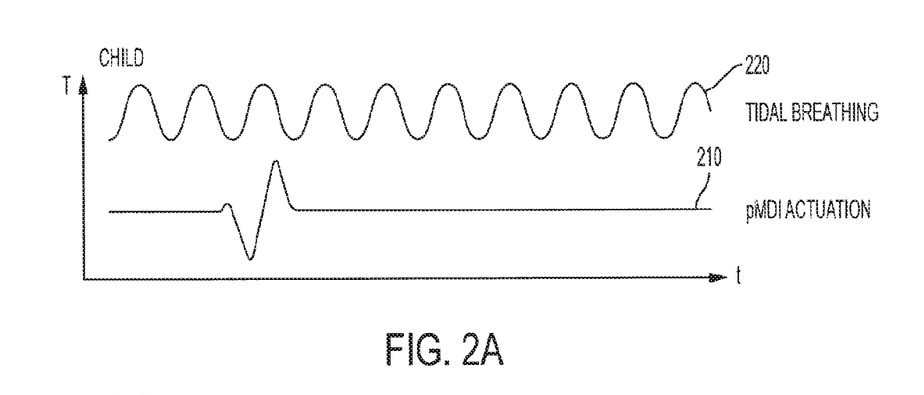
FIG. 2A is a diagram showing temperature changes when a device of the present disclosure is being used by a child.
Figure 2B:
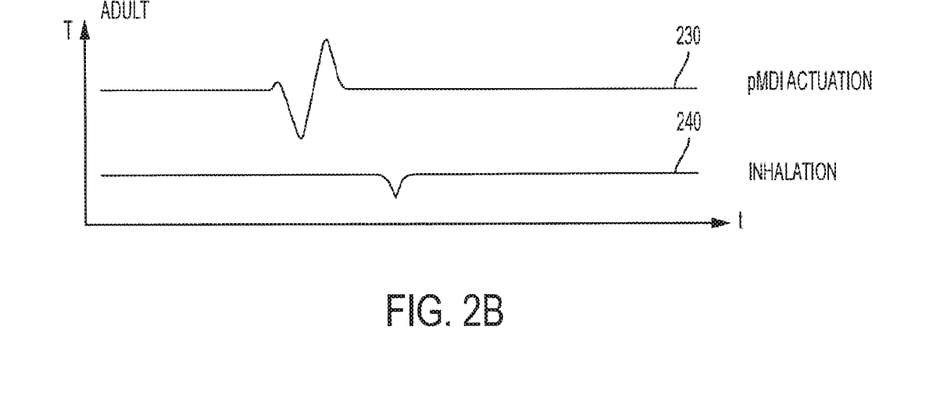
FIG. 2B is a diagram showing temperature changes when a device of the present disclosure is being used by an adult.

FIGS. 2A and 2B depict waveforms or traces indicating temperature changes in the chamber. FIG. 2A shows the temperature changes when a child (a person whose lungs are developed sufficiently to inhale deeply and clear the spacer in one breath, such as someone who is about 4 years of age or less) uses the pulmonary delivery device 110. When the lungs of the person are sufficiently developed so that he or she can breathe deeply and clear the spacer in one breath, the pattern is different. For example, FIG. 2B shows the temperature changes when an adult uses the pulmonary delivery device 110.

As shown in FIG. 2A, the waveform 220 represents the changes in temperature when the patient is breathing in and out of the spacer through the facemask. The waveform 220 is marked tidal breathing. The waveform 210 represents the actuation of the pressurized metered dose inhaler into the valved holding chamber device, which causes an initial cooling of the chamber that is followed by a rebound transient increase in temperature. These waveforms show that the patient was breathing in and out from the spacer when the pressurized metered dose inhaler was actuated into the valved holding chamber and that the patient continued to breathe in and out of the device for several breaths. At this time, it is normally considered that the chamber 122 is empty of the medication and the medication has been successfully delivered. A feedback signal, which is representative of the successful delivery of the medication, is accordingly generated and transmitted to a processor for the purpose of monitoring the patient's adherence to the prescribed regimen. For example, a temperature drop as depicted by the first waveform 210 can be used for generating the feedback signal for indicating the initial actuation of the medication into the chamber 122, which is caused by propellant evaporation. The tidal form of the second waveform 220 can also be utilized, in addition to or in place of the temperature drop of the first waveform 210, for generating the feedback signal. The other fact is that young children may be asked to breathe in and out from the spacer until they are old enough to inhale deeply and clear the spacer in one breath.

As shown in FIG. 2B, a third waveform 230 shows the temperature changes when the pulmonary delivery device 110 is initially actuated by an adult. A fourth waveform 240 shows the temperature changes as the adult patient inhales from the device, which is normally a single deep breath, from the chamber 122 following the actuation of the pulmonary delivery device. At this time, it is normally considered that the chamber 122 is empty of the medication and the medication has been successfully delivered. A feedback signal, which is representative of the successful delivery of the medication, is accordingly generated and transmitted to a processor. For example, a temperature drop as depicted by the third waveform 230 can be used for generating the feedback signal for indicating the initial actuation of the medication into the chamber 122, which is caused by propellant evaporation. Another temperature drop, which is short but highly reproducible as depicted by the fourth waveform 240 that corresponds to a temperature drop due to inhalation, can be utilized for generating the feedback signal, in addition to or in place of the temperature drop of the third waveform 230.

Figure 3A:
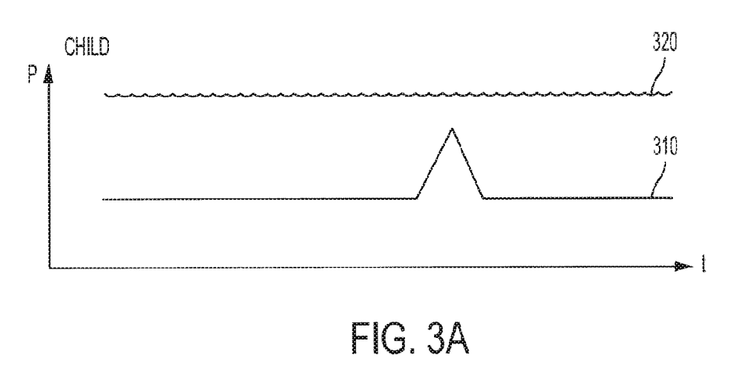
FIG. 3A is a diagram showing pressure changes when a device of the present disclosure is being used by a child.
Figure 3B:
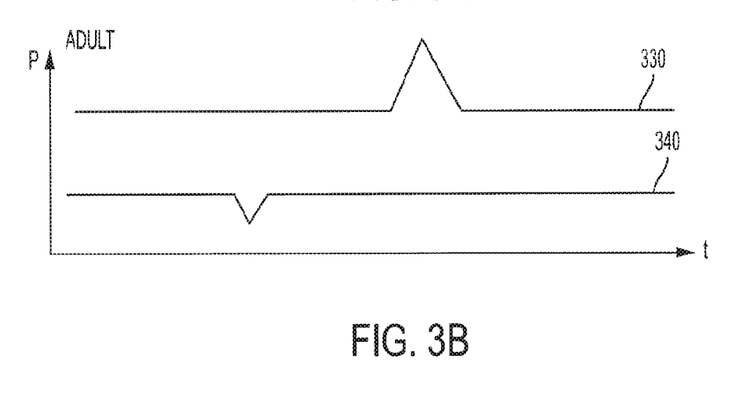
FIG. 3B is a diagram showing pressure changes when a device of the present disclosure is being used by an adult.

FIGS. 3A and 3B depict waveforms indicating pressure changes in the chamber. FIG. 3A shows the pressure changes when a child, as defined hereinabove, uses the pulmonary delivery device 110. Just as respects the temperature pattern, when the lungs of the person are sufficiently developed so that he or she can breathe deeply and clear the spacer in one breath, the pressure pattern is different. For example, FIG. 3B shows the pressure changes when an adult uses the pulmonary delivery device 110.

As shown in FIG. 3A, a first waveform 310 shows the pressure changes when the pulmonary delivery device 110 is initially actuated by the child or a care giver when the child is too young to actuate the pressurized metered dose inhaler by himself of herself. A second waveform 320 shows the pressure change as the child continue to breathe from the chamber 122 following the actuation of the pulmonary delivery device for at least several breaths. At this time, it is normally considered that the chamber 122 is empty of the medication and the medication has been successfully delivered. A feedback signal, which is representative of the successful delivery of the medication, is accordingly generated and transmitted to a processor. For example, a pressure jump as depicted by the first waveform 310 can be used for generating the feedback signal for indicating the initial actuation of the medication into the chamber 122. The form of second waveform 320 can also be utilized, in addition to or in place of the pressure jump of the first waveform 310, for generating the feedback signal. On the other hand, the waveform 320 indicates that the pressure signal is not sufficient when a child breathes through the device to give a meaningful report. Background noise may also contribute to this.

As shown in FIG. 3B, a third waveform 330 shows the pressure changes when the pulmonary delivery device 110 is initially actuated by the adult. A fourth waveform 340 shows the pressure changes as the adult continue to breathe, which is normally a single deep breath, from the chamber 122 following the actuation of the pulmonary delivery device. At this time, it is normally considered that the chamber 122 is empty of the medication and the medication has been successfully delivered. A feedback signal, which is representative of the successful delivery of the medication, is accordingly generated and transmitted to a processor. For example, a pressure jump as depicted by the third waveform 330 can be used for generating the feedback signal for indicating the initial actuation of the medication into the chamber 122. In addition, a slight pressure drop as depicted by the fourth waveform 340 can also be utilized for generating the feedback signal, which represents the patient inhalation from the device.

Although temperature sensors and pressure sensors have been described above, it should be understood that other parameters and their associated sensors can be used to replace or supplement the temperature and pressure sensors, which include, but is not limited to, changes in concentration and/or density of carbon dioxide and other gases, such as nitric oxide, oxygen or nitrogen, and the like; motion sensors (including but not limited to sensors for detecting linear motions, angular motions and/or vibrations); humidity sensor; optical sensors; acoustic sensors; and/or vibration sensors.

In addition, the various measurements of the different sensors can be combined or modified in a strategic manner for generating the feedback signals for the purpose of monitoring the patient's adherence to the prescribed treatment. For example, a rise in pressure that occurs on actuation of the drug into the chamber can be measured; a drop in pressure on deep inhalation from the chamber can be measured to indicate that the adult has inhaled from the chamber. Thus, the time between actuation of the drug entry into the chamber and the inhalation from the chamber can be measured. As a result, a successful use of the pulmonary delivery device can be documented, when for example, less than 10 seconds has elapsed between the actuation and the inhalation. A light associated with the monitor device can be turned on for 2 second accordingly. Other feedback systems for example, a noise, LCD screen display or vibration can be used to feed back.

Furthermore, a reduction in temperature can be measured as an indicator of actuation into the chamber, and a reduction of pressure the chamber can be detected as an indicator of inhalation from the chamber.

In addition, a temperature decrease and/or a pressure increase can be measured as an indicator of actuation into the chamber, and inhalation from the chamber can be indicated by the measurement of a temperature drop in the mouthpiece (or chamber) during full inspiration.

The different sensors, such as the temperature sensors and the pressure sensors, can be placed at different locations on the chamber and/or the facemask, for the purpose of achieving desirable sensitivity.

Figure 4:
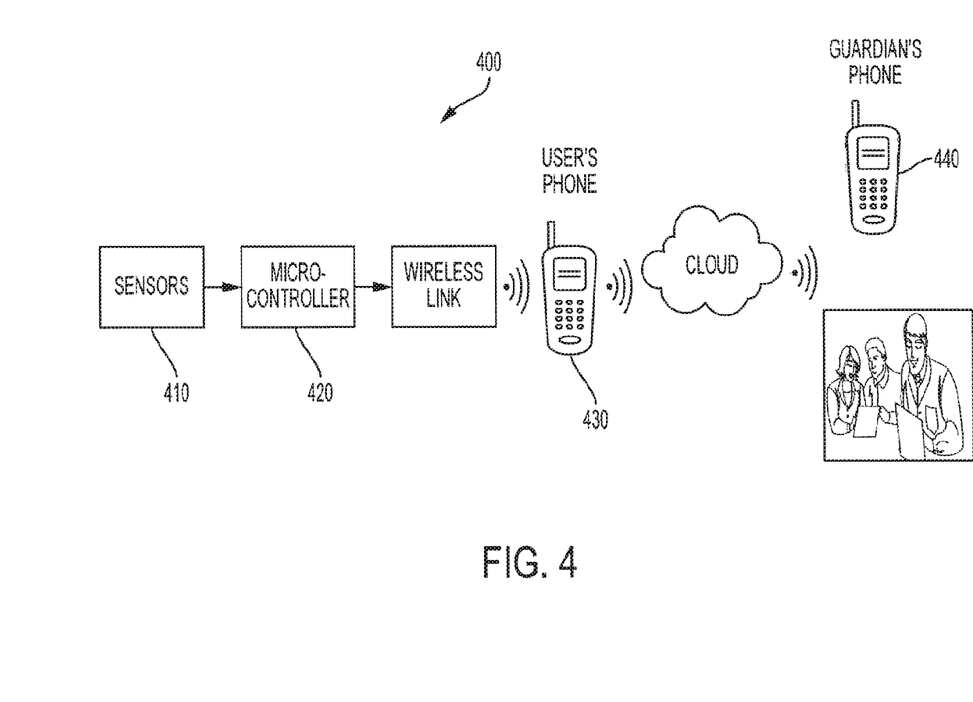
FIG. 4 shows a monitoring system according to another embodiment of the disclosure.

The feedback signals, including the temperature signals and the pressure signals, are transmitted and processed by a processor. The signal transmission can be implemented by any wired or wireless connection. The processor can be any suitable microprocessor, CPU, MPU, computer or workstation. The processor can be in communication with a processing center (such as, a computer of a hospital for monitoring patients' drug adherence) and/or one or more user terminal equipments (such as, a smart phone of a patient, a patient's family member or a doctor or nurse). A representative monitoring system 400 is shown in FIG. 4, which includes sensors 410, a microcontroller 420, a first user terminal equipment 430 in communication with the microcontroller 420 through wireless link, and a second terminal equipment 440 in communication with the first user terminal equipment 430 through cloud communications. The first user terminal equipment 430 can be a patient's smart phone and the second user terminal equipment 440 can be a smart phone of the patient's guardian or caregiver.

Figure 5:
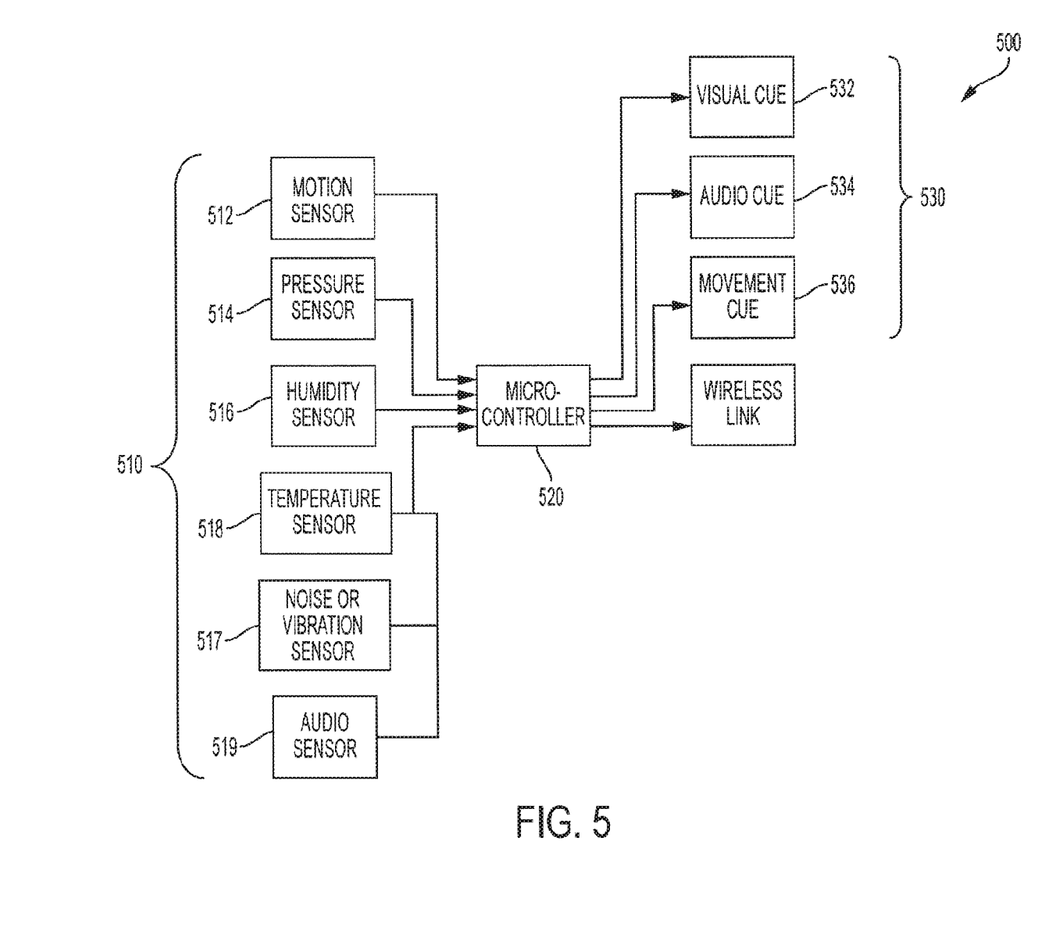
FIG. 5 shows a monitoring system according to yet another embodiment of the disclosure.

FIG. 5 is a diagram of a monitoring system 500 according to an exemplary embodiment of the present application. The monitoring system 500 includes a sensor array 510, which includes a motion sensor 512, a pressure sensor 514, a humidity sensor 516, a noise or vibration sensor 517, a temperature sensor 518 and an audio sensor 519. The sensor array 510 generates feedbacks signals based on the detection results of the various sensors. The monitoring system 500 further includes a microcontroller 520, which receives and processes the feedback signals to generate control signals. The monitoring system 500 further includes an indicator unit 530, which receives the control signals and generates indicators. The indicator unit 530 includes a visual indicator subunit 532, an audio indicator subunit 534, and a movement indicator subunit 536. The visual indicator subunit 532 can output a visual signal, such as blinking of an LED. The audio indicator subunit 534 can output an audio signal, such as a beeping sound. The movement indicator subunit 536 can output a motion signal, such as a vibration.

Figure 6:
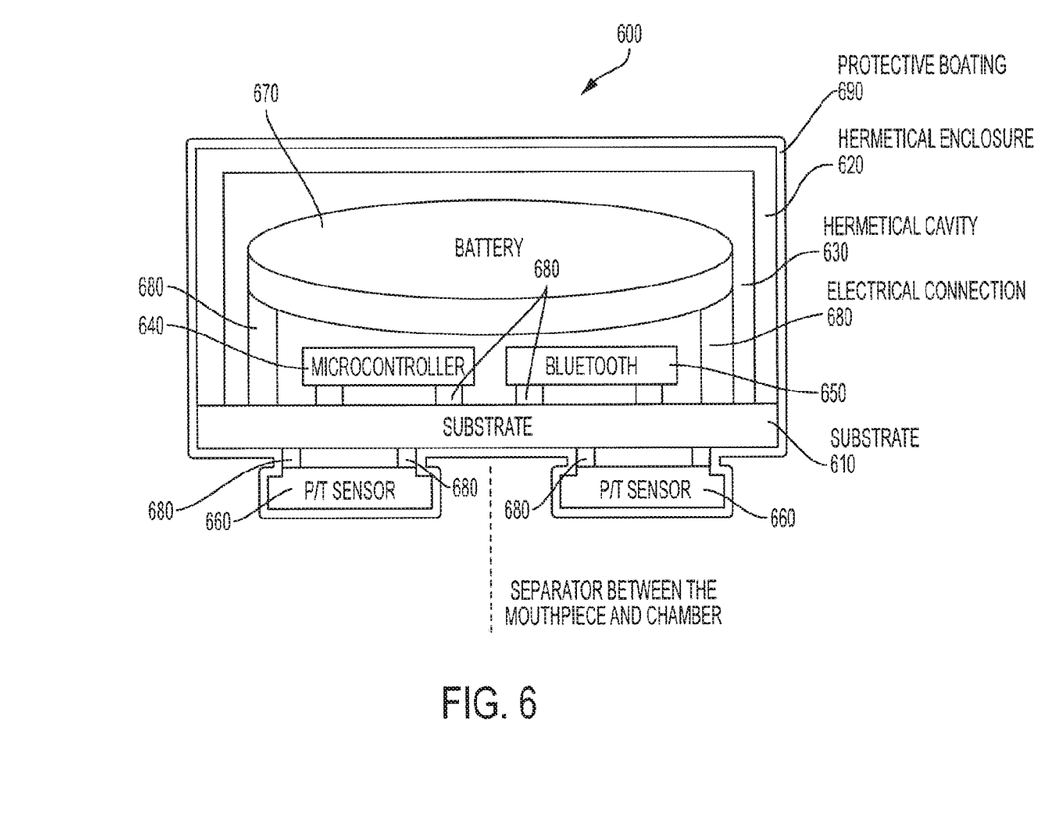
FIG. 6 is a diagram showing a sensor of the monitoring device of FIG. 1A.

FIG. 6 is a diagram showing a sensor array 600 according to another exemplary embodiment of the present application. The sensor array 600 includes a substrate 610, on which a hermetical enclosure 620 is formed. The substrate 610 and the hermetical enclosure 620 together define a hermetical cavity 630. On the top surface of the substrate 610, within the hermetical cavity 630, a microcontroller 640 and a wireless link 650 are formed through a suitable semiconductor fabricating process. On the bottom surface of the substrate 620, outside of the hermetical cavity 630, a plurality of sensors 660 are formed through a suitable semiconductor fabricating process. A battery unit 670 is also formed within the hermetical cavity 630 for powering the microcontroller, the wireless link and the sensors. Numerous electrical connections 680 are formed to provide electrical connections between the other components. A protective coating 690 is also formed to seal the sensor array and to protect the sensor array from water and other contaminates from breath.

Figure 7:
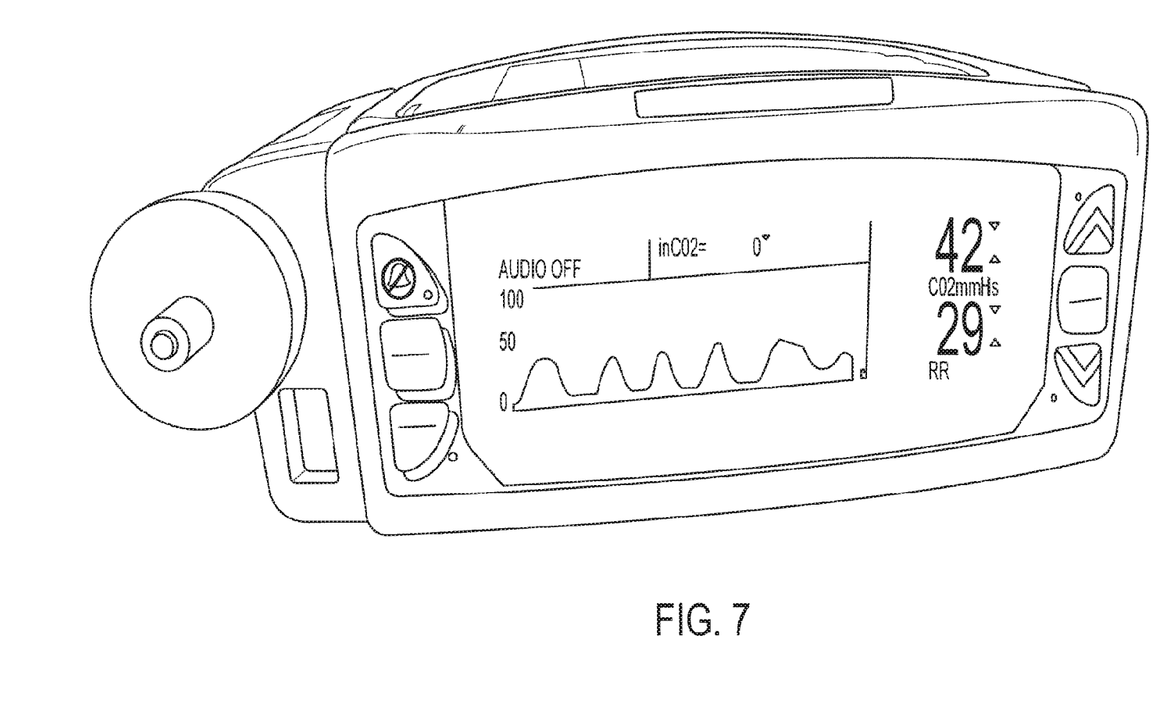
FIG. 7 is a receiving device which monitors and records changes of the level of carbon dioxide exhaled by a patient, according to still another embodiment of the disclosure.

According to another embodiment of the present disclosure, breathing gas (particularly, expiratory gas) of a patient is analyzed to determine and promote adherence of the patient to the prescribed regimen. For example, a sensor for detecting the existence and/or level of carbon dioxide can be provided to the drug dispenser 130, which can be a mouthpiece or a mask. Alternatively, the sensor 140 can optionally include the carbon dioxide ($CO_2$) sensor. FIG. 7 depicts a monitor which receives and detects the signal provided by the sensor and records the waveforms or traces for indicating $CO_2$ level changes when the patient breathes to take the drugs. Other gases can also be measured in a similar way, including Nitric oxide, Oxygen or Nitrogen.

Figure 8:
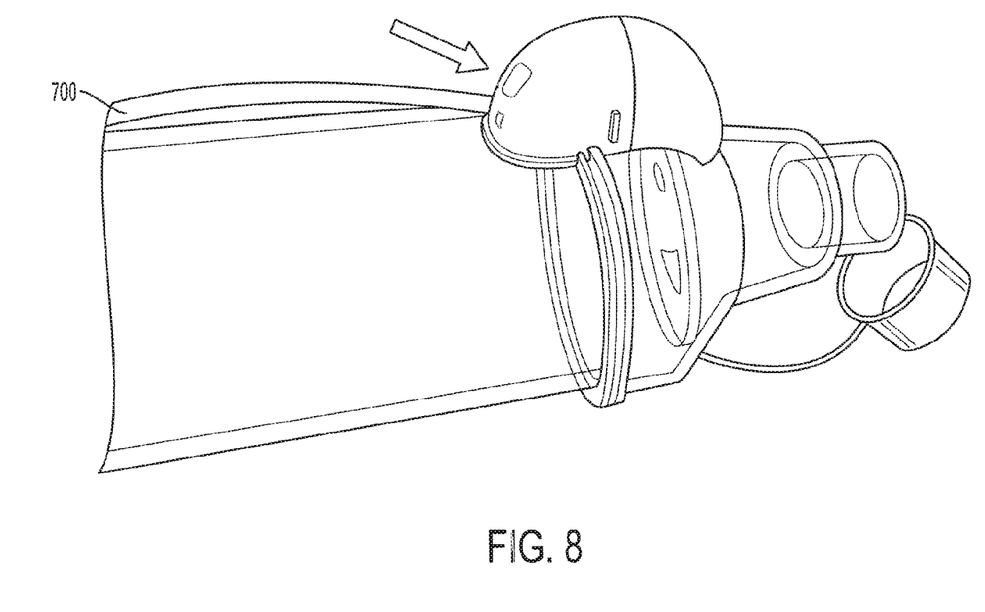
FIG. 8 is a diagram showing a device for monitoring adherence to an inhaled therapy, according to still yet another embodiment of the present disclosure.

FIG. 8 depicts another embodiment of the present disclosure. In this embodiment, the device 100 further includes a measurement tube 700. The measurement tube 700 is coupled to the adapter 120 or the drug dispenser 130 to be in fluid communication with the interior of the adapter 120 or the drug dispenser 130. The device 100 can optionally include a collection bag or system (not shown). The expiratory gas of the patient can be channeled through the tube 700 into the collection bag or system for additionally analyzing and/or sampling the gas or other materials exhaled by the patient. For example, the collected gas and materials can be analyzed through mass spectroscopy or nitric oxide, using techniques known to the skilled artisan.

Additionally or alternatively, a filter or similar porous material can be provided at an exit of the adapter 120, which allows collection of exhaled particles and other materials from the patient. The particles and materials collected by the filter or similar porous material can be analyzed to identify the pathogen or constituents (such as, bacteria, viruses, fungi, bacteriophages, inflammatory cells and mediators and the like) of the expiratory gas of the patient. The patient can be asked to breathe out quietly from the device or to cough through the device, to generate particles for subsequent analysis.

According to another aspect of the present disclosure, an accelerometer can be included in the device. The accelerometer allows detection of appropriate shaking of the pressurized metered dose inhaler prior to actuation. In use, the patient shakes the pressurized metered dose inhaler within a defined time frame (for example, in a few seconds) to actuate the pressurized metered dose inhaler into the spacer.

According to still another aspect of the present disclosure, analysis of the breath pattern of the patient (such as, the breathing pattern of the inspiratory and expiratory times of the breath) can be performed by processing the signals.

According to yet another aspect of the present disclosure, the device allows detection of aerosol added in to it as a dry powder, from a nebulizer for system other than a pressurized metered dose inhaler that delivers aerosol containing drug into the spacer.

In addition, the device of the present disclosure can be used to detect noise of the actuation and the noise of the valve opening and airflow through the device. The device can also detect the noise of the inspiratory flow indicator that is built into the spacer.

The device of the present disclosure can use Bluetooth technology to expand the utilization of the device. This allows determination of whether bronchodilator or prophylactic drug has been used through the device. The specific acoustic, pressure and temperature signature of different pMDIs will be determined so the device can recognize if the drug used is a bronchodilator, inhaled corticosteroid or other drugs (e.g. combination medications) administered via the spacer. This also allows determination of the strength of a specific pMDI for example, between 50, 100 or 250 micrograms of fluticasone propionate.

If the patient is using a bronchodilator, the patient can indicate this by pressing a button/surface of the device. This allows use of bronchodilator therapy to be monitored.

The device of the present disclosure can detect the pressure and temperature generated from the prescribed drug and drug strength. By doing this, it will be able to determine from the signal received if a bronchodilator or a corticosteroid (or other drug) has been delivered. This may be particularly interesting to a specific pMDI manufacturer.

As the device is able to sense the actuation of the drug into the space chamber, it will be able to count the number of actuations over the long term. If being interpreted appropriately, such count information can indicate whether the spacer is being overused and/or whether the drug canister needs to be replaced or refilled.

While the fundamental novel features of the disclosure as applied to various specific embodiments thereof have been shown, described and pointed out, it will also be understood that various omissions, substitutions and changes in the form and details of the devices illustrated and in their operation, may be made by those skilled in the art without departing from the spirit of the disclosure. For example, it is expressly intended that all combinations of those elements and/or method steps which perform substantially the same function in substantially the same way to achieve the same results are within the scope of the disclosure. Moreover, it should be recognized that structures and/or elements and/or method steps shown and/or described in connection with any disclosed form or embodiment of the disclosure may be incorporated in any other disclosed or described or suggested form or embodiment as a general matter of design choice. It is the intention, therefore, to be limited only as indicated by the scope of the claims appended hereto.

The invention claimed is:

1. A device for monitoring adherence of a patient to a prescribed regimen,
the device comprising:
a pulmonary delivery device comprising a pressurized cartridge for accommodating a drug according to the prescribed regimen and a nozzle through which the drug is released;
an adapter comprising an inlet, an outlet and a chamber between the inlet and outlet, wherein the inlet is in fluid communication with the nozzle for admitting the drug into the chamber, wherein the chamber is defined by a hollow wall;
a dispenser coupled with the adapter for allowing the drug to enter the dispenser from the chamber; and
at least one sensor for detecting a parameter change associated with a movement of the drug from the pulmonary delivery device to the dispenser and generating a feedback signal based on the parameter change, wherein the feedback signal is processed for generating an indicator signal representative of delivery of the drug to the patient,
wherein the sensor comprises:
a substrate:
a hermetical enclosure formed on a top surface of the substrate, wherein the substrate and the hermetical enclosure together defines a hermetical cavity;
a microcontroller and a wireless link formed on the top surface of the substrate and within the hermetical cavity;
a plurality of sensor units formed on a bottom surface of the substrate and outside of the hermetical cavity;
a battery unit formed within the hermetical cavity for powering the microcontroller, the wireless link and the plurality of sensors; and
a protective coating for sealing the substrate, the hermetical enclosure, the microcontroller, the wireless link, the plurality of sensor units and the battery unit.

2. The device according to claim 1, wherein the sensor comprises at least one of a temperature sensor for detecting a temperature change in the adapter or the dispenser, a pressure sensor for detecting a pressure change in the adapter or the dispenser, a motion sensor for detecting a movement of the adapter or the dispenser, a humidity sensor for detecting a humidity change in the adapter or the dispenser, and a gas sensor for detecting change of density and/or concentration of a gas component in the adapter or the dispenser.

3. The device according to claim 1 or 2, further comprising a processor for processing the feedback signal and generating the indicator signal, wherein the indicator signal comprises at least one of a visual signal, an audio signal and a movement signal.

4. The device according to claim 3, further comprising a first terminal device used by the patient, wherein the first terminal device is in communication with the processor for receiving the indicator signal.

5. The device according to claim 4, further comprising a second terminal device used by a medical professional or appropriately trained individual, wherein the second terminal device is in communication with the processor for receiving the indicator signal.

6. The device according to claim 1, wherein the sensor is mounted to the hollow wall of the chamber.

7. The device according to claim 1, wherein the sensor comprises a temperature sensor configured to chronologically detect a first temperature change and a second temperature change, wherein the first temperature change meets a first predetermined pattern and the second temperature change meets a second predetermined pattern.

8. The device according to claim 7, wherein the first predetermined pattern comprises a decrease of a temperature within the adapter or the dispenser followed by an increase of the temperature, wherein the second predetermined pattern comprises a continuous waveform.

9. The device according to claim 7, wherein the first predetermined pattern comprises a decrease of a temperature within the adapter or the dispenser followed by an increase of the temperature, wherein the second predetermined pattern comprises a decrease of the temperature.

10. The device according to claim 1, wherein the sensor comprises a pressure sensor configured to chronologically detect a first pressure change and a second pressure change, wherein the first pressure change meets a first predetermined pattern and the second pressure change meets a second predetermined pattern.

11. The device according to claim 10, wherein the first predetermined pattern comprises an increase of a pressure within the adapter or the dispenser followed by a decrease of the pressure, wherein the second predetermined pattern comprises a continuous pressure with no substantial changes.

12. The device according to claim 10, wherein the first predetermined pattern comprises an increase of a pressure within the adapter or the dispenser followed by a decrease of the pressure, wherein the second predetermined pattern comprises a decrease of the pressure followed by an increase of the pressure.

13. The device according to claim 1, wherein the dispenser comprises a facemask comprising a continuous edge configured to follow a facial contour of the patient face and an inlet coupled with the outlet of the adapter for allowing the drug to enter the facemask from the chamber.

14. The device according to claim 1, wherein the dispenser comprises a mouthpiece comprising an inlet coupled with the outlet of the adapter for allowing the drug to enter the mouthpiece from the chamber.

15. The device according to claim 1, wherein the sensor comprises a carbon dioxide sensor for detecting change of the level of carbon dioxide in the adapter or the dispenser.

16. The device according to claim 1, further comprising a measurement tube and a gas collection system, wherein the measurement tube is coupled to the adapter or the dispenser to be in fluid communication with the interior of the adapter or the dispenser, wherein the expiratory gas of the patient is channeled to the collection system through the measurement tube.

17. The device according to claim 1, further comprising a filter for collecting particles from the expiratory gas of the patient, wherein the collected particles are analyzed to identify pathogens or constituents of the expiratory gas of the patient.

* * * * *